(12) United States Patent
Vigano' et al.

(10) Patent No.: US 7,425,648 B2
(45) Date of Patent: Sep. 16, 2008

(54) PROCESS FOR THE PREPARATION OF NATEGLINIDE, PREFERABLY IN B-FORM

(75) Inventors: Enrico Vigano', Lurago D'Erba (IT); Enrica Pizzatti, Poggiridenti (IT); Simona Lanfranconi, Montano Lucino (IT); Renato Molteni, Inverigo (IT); Ernesto Landonio, Rescaldina (IT)

(73) Assignee: A.M.S.A. Anonima Materie Sintetiche E. Affini S.p.A., Milan (IT)

( * ) Notice: Subject to any disclaimer, the term of this patent is extended or adjusted under 35 U.S.C. 154(b) by 516 days.

(21) Appl. No.: 11/028,283

(22) Filed: Jan. 3, 2005

(65) Prior Publication Data

US 2006/0148902 A1    Jul. 6, 2006

(51) Int. Cl.
C07C 229/00    (2006.01)

(52) U.S. Cl. .................. 562/450; 562/444; 562/445

(58) Field of Classification Search .................. 514/563; 562/450, 444, 445
See application file for complete search history.

(56) References Cited

U.S. PATENT DOCUMENTS 5,488,150 A    1/1996   Sumikawa et al.

FOREIGN PATENT DOCUMENTS

| EP | 01 96 222 B1 | 1/1992 |
| EP | 0 526 171 A2 | 2/1993 |
| EP | 1 334 962 A1 | 8/2003 |
| EP | 1 334 963 A1 | 8/2003 |
| EP | 1 334 964 A1 | 8/2003 |
| JP | 2969397 B | 11/1999 |

*Primary Examiner*—Taylor Victor Oh
(74) *Attorney, Agent, or Firm*—Stetina Brunda Garred & Brucker

(57) ABSTRACT

The present invention relates to a process for the preparation of nateglinide, preferably in B-form, substantially free from the H-form, comprising three steps starting from D-phenylalanine methyl ester or a salt thereof.

22 Claims, 13 Drawing Sheets

PROCESS FOR THE PREPARATION OF NATEGLINIDE, PREFERABLY IN B-FORM

CROSS-REFERENCE TO RELATED APPLICATIONS

Not Applicable

STATEMENT RE: FEDERALLY SPONSORED RESEARCH/DEVELOPMENT

Not Applicable

FIELD OF THE INVENTION

The present invention relates to a process for the preparation of nateglinide, useful as antidiabetic agent, in high yields, and preferably for the preparation of nateglinide in B form substantially free from nateglinide in H form.

STATE OF THE ART

Nateglinide, i.e. the N-(trans-4-isopropylcyclohexylcarbonyl)-D-phenylalanine, is known for having a hypoglycemic action, and used therefore for preparing pharmaceutical compositions for treating diabetes.

It is known that, when nateglinide is prepared on industrial scale, there may occur the risk that the crystalline product obtained contains more coexisting polymorph crystals, the B-form crystals and the H-form crystals.

Given that the pharmaceutical use requires to have available nateglinide in a single crystalline form, not contaminated by other forms of polymorph crystals; many efforts have been made to have available a scalable process, which is suitable for preparing a single crystalline form of nateglinide.

The European Patent No. 196 222 discloses for the first time certain D-phenylalanine derivatives having hypoglycemic action, including nateglinide. A process for the preparation of nateglinide is therein described, comprising a condensation with dicyclohexylcarbodiimide to obtain trans-4-isopropylcyclohexane carboxylic acid N-hydroxysuccinimide ester, which is then reacted with D-phenylalanine methyl ester hydrochloride to obtain the nateglinide methyl ester. Starting from the methyl ester, nateglinide sodium salt is formed in aqueous sodium hydroxide and methanol, nateglinide is then precipitated by acidification with hydrochloric acid and a recrystallisation from methanol-water is carried out to yield the nateglinide. Besides having a low yield, this process is unsuitable to be scaled up, particularly because of the use of the expensive condensing agent. Moreover, as far as the problem of polymorphism of crystalline nateglinide is concerned, in EP No. 196 222 no reference is made to the crystalline form of the so obtained nateglinide, but, according to what has been stated later in EP No. 526 171, the use of the mixture methanol/water gives a nateglinide in the B-form. However, it was discovered still later (see EP No. 1 334 964) that often, in particular during industrial scaling-up, the B-form so obtained was contaminated by the H-form. Moreover, in the synthesis according to EP No. 196 222, the last recrystallization step harbours the risk of re-esterification of the product already obtained, such that the nateglinide resulting from the overall process is often contaminated by a non negligible amount of the nateglinide methyl ester.

The European Patent Application No. 1 334 962 refers instead to a process for producing nateglinide by Schotten Baumann reaction, comprising reacting isopropylcyclohexylcarbonyl chloride with phenylalanine and potassium hydroxide in water and an organic solvent miscible with water to give a potassium salt of nateglinide. According to EP-A No. 1 334 962 nateglinide free from the impurity that usually forms in this reaction, i.e. from the dimeric product isopropylcyclohexylphenylalanine-phenylalanine (IPP), is obtained, provided that very careful control of the reaction conditions is carried out, but the authors of EP-A No. 1 334 962 are silent about yield and the more general purity degree of the end-product. The thus obtained nateglinide is in fact contaminated with almost 10% by weight of isopropylcyclohexylcarboxylic acid, and this impurity, besides being laborious to eliminate, represents also a precursor of nateglinide having a specific isomeric structure, i.e. a valuable compound not to be wasted. Moreover, in EP-A No. 1 334 962, no reference is made to the crystalline form of nateglinide actually obtained.

The European Patent Application No. 1 334 964 discloses a process for producing B-form nateglinide crystals free from crystals of the H-form, comprising drying solvated wet crystals of nateglinide at a temperature lower than 50° C. until an amount of solvent lower than 5% remains, then heating the solvated wet crystals at 60 to 110° C. to make the conversion from H-form into B-form. The yield of this process is nevertheless very low: in the single example reported in EP 1 334 964 the yield is 54.3%.

The Japanese Patent No. 2969397 discloses a process for preparing N-long chain acyl beta alanine compounds comprising reacting the beta-alanine with the fatty acid halide and potassium hydroxide to obtain the potassium salt of a N-long chain acyl beta-alanine, which is then treated with a strong acid at a temperature comprised between 60 and 90° C., to obtain the N-long-chain beta-alanine. According to the Japanese Patent No. 2969397 the high temperature during the treatment with the strong acid, is essential to control the size of the crystals so that they form of uniform size and their filtration may be improved. No reference is made to the form of the so obtained crystals.

In view of the above, the need of a process for preparing nateglinide in high yields and with high purity, preferably in B-form free from nateglinide in H form, which does not possess the above said drawbacks of the prior art processes, is still deeply felt. In particular, there is the need for a process which leads directly and in good yields to a nateglinide of pharmaceutical grade, requiring no further chemical purification.

BRIEF SUMMARY OF THE INVENTION

The Applicant has now found a process, which is scalable and allows providing with high yields nateglinide free from the by-products formed by the prior art process, and preferably in B-form, not contaminated by nateglinide in H-form.

Importantly, the nateglinide preparations directly resulting from the process invented by the Applicant are of pharmaceutical grade and do therefore not require any re-crystallization step. The former is an important aspect, since, as outlined above, the known recrystallizations of nateglinide with water/methanol mixtures may bring about a measurable contamination with the corresponding methyl ester. Applicant has indeed found that the tendency of the nateglinide to esterify (a sample of nateglinide at reflux for 8 hours in a 1:1 mixture of water and methanol undergoes an esterification of 9%) is non-negligible even at markedly lower temperatures. Moreover, the treatment of nateglinide with various solvents and with various water/solvent mixtures adapted for re-crystallization often leads to a gel-formation rendering extremely difficult and laborious the handling of the nateglinide preparation during the re-crystallization step, especially on industrial scale where such pronounced tendency to gel-formation may even hamper the quantitative recovery of the product from the reactor. This is because addition of a suitable solvent to a nateglinide preparation often causes its swelling/gelling such that increased volumes of solvent are required to get a nateglinide solution of reasonable viscosity. In turn, the higher the dilution of the nateglinide solutions thus obtained, the more difficult or laborious becomes the task of re-recrystallizing the product achieving acceptable yields. It is therefore highly desirable to provide a synthesis leading directly to a nateglinide of pharmaceutical grade, without any need of a final re-crystallization of the end product.

Another problem arising with the re-crystallization of nateglinide from organic solvents or from mixtures of organic solvents with water is the stringent control of conditions which is imperative to obtain the quantitative formation of the desired crystal form. It appears indeed that the solvated wet crystals of nateglinide obtained according to EP 1 334 964, i.e. by dissolving nateglinide within an organic solvent or with aqueous dilutions of organic solvents require at least two measures to arrive at the desired result, namely cooling down to 10° C. to obtain the proper solvated wet crystals, which are then in turn subjected to a defined drying profile. According to what is stated in EP 1 334 964, this applies to both, the solvates with ethanol obtained from 60% aqueous ethanol containing 5 wt % nateglinide, as well as to the so-called hydrates which are obtained instead through the addition of water to an ethanolic solution of nateglinide.

Hence, there was a stringent need in the art for providing a process overcoming the problems arising with the known methods of re-crystallisation.

Subject of the present invention is therefore a process for the preparation of nateglinide, comprising the following steps:

i) reaction in a first organic solvent between D-phenylalanine methyl ester or a salt thereof, trans 4-isopropylcyclohexancarboxylic acid and an acyl chloride or carbonyldiimidazol, to obtain the nateglinide methylester;

ia) optionally isolating the nateglinide methylester thus obtained and re-dissolving the nateglinide methylester in a second organic solvent, to give a solution, ii) addition of water and alkali hydroxide to the reaction mixture coming from step i) without isolating the nateglinide methyl ester, or, if applicable, to the solution of step ia) and separation of the aqueous phase containing the alkali salt of nateglinide;

iii) addition of hydrochloric acid to the aqueous phase coming from step ii), to obtain nateglinide, wherein the organic solvent actually employed in step ii) is a solvent non-miscible with water.

With the process of the present invention, it is possible to obtain nategelinide in B-form, substantially free of H-form, provided that the precipitation according to step iii) is carried out at room temperature, more preferably at a temperature between 5° C. and 20° C.

Further subject of the invention is a process for the preparation of nateglinide in B-form substantially free from H-form, starting from nateglinide not being in the pure B-form, e.g. being in B-form contaminated with nateglinide in H-form in various proportions.

Features and advantages of the present invention will be illustrated in detail in the following description.

BRIEF DESCRIPTION OF THE DRAWINGS

The invention as described within the frame of the present Application may be better understood with reference to the enclosed Figures, in which:

FIG. 11 is a X-ray powder diffractogram recorded with the a pure preparation of nateglinide B-form obtained according to the present invention, whereas

DETAILED DESCRIPTION OF THE INVENTION

Figure 1:
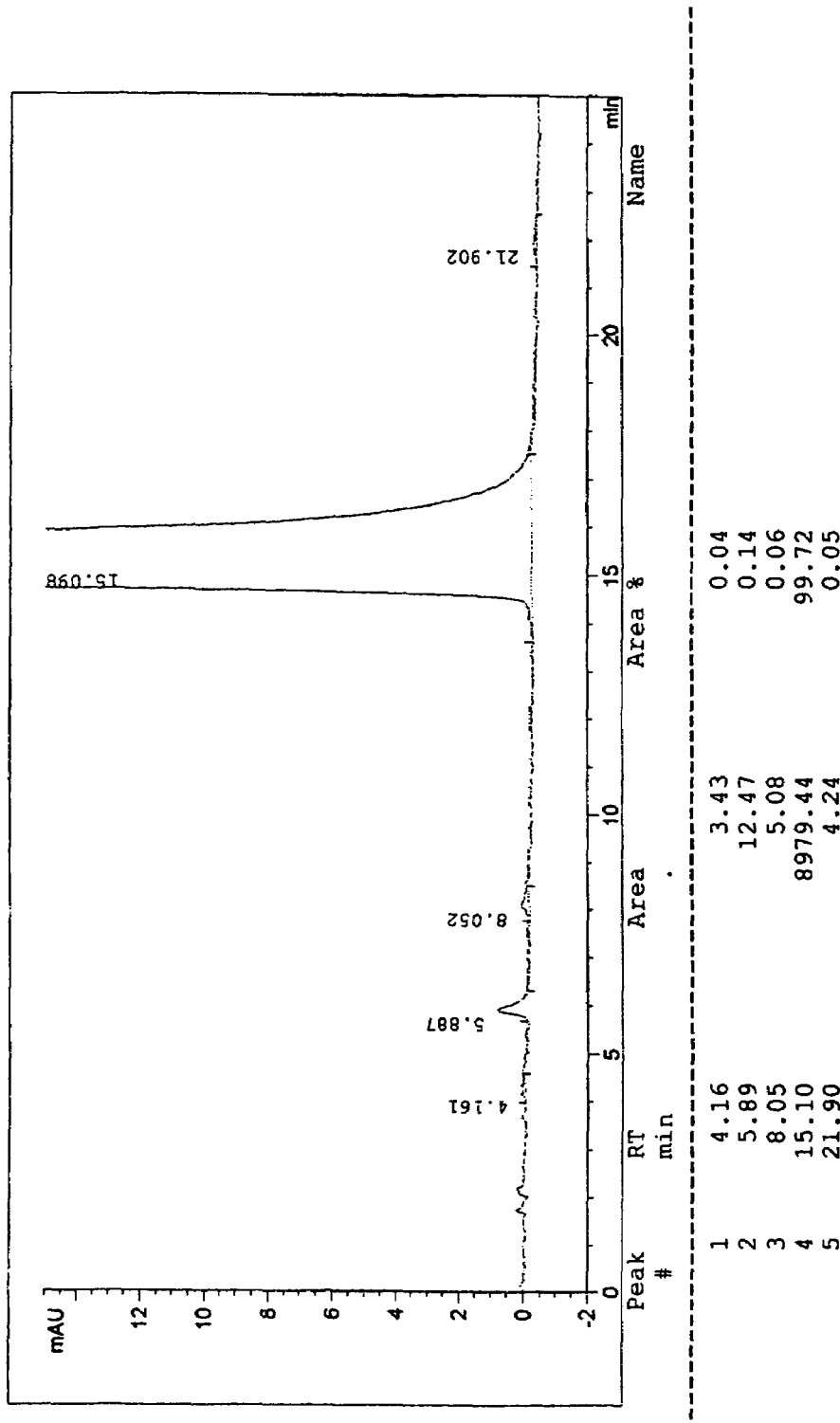
FIG. 1 is a HPLC chromatogram of nateglinide methyl ester.

As will be shown herein later, the preparations of nateglinide obtained according to the present invention, and in particular according to claim 1, are characterized by a high chemical yield and a high chemical purity. Preferably, also high polymorphic purity can be achieved.

According to the present invention, the temperature during the addition of water and alkali hydroxide and the separation of the aqueous phase containing the alkali salt of nateglinide in step ii), preferably ranges from 45 to 55° C.

On the other hand, during the precipitation in subsequent step iii), polymorphic mixtures of the H-form and the B-form are obtained, if step iii) is carried out at a temperature higher than room temperature. The polymorphic mixture thus obtained (which benefits already from the high chemical yield and high chemical purity) can be transformed later into the pure B-form with the method herein described or, if desired, into any other polymorphic form of nateglinide described in the art through the adoption of adequate measures likewise described in the art. However, if preferred, a preparation of pure B-form, substantially free from the H-form of nateglinide may also be provided directly by the process of the present invention, namely if the temperature during precipitation of the nateglinide with hydrochloric acid in step iii) is maintained at room temperature or lower, e.g. in the range from 5° C. to 20° C., preferably from 10° C. to 20° C. and more preferably from 15° C. to 20° C.

The first organic solvent employed in step i) can be a water-miscible organic solvent or an organic solvent non-miscible with water. In any case, the first organic solvent must be compatible with the chemical reaction of step i), i.e. it must be inert. According to the present invention, a water-miscible organic solvent is a solvent of which 100 ml, at a temperature of 20° C. may dissolve at least 0.5 g, preferably at least 0.1 g and more preferably at least 0.05 g of water or vice versa (i.e. 100 ml of water may dissolve at least 0.5 g, more preferably at least 0.1 g and more preferably at least 0.05 g of solvent). Hence, according to the present invention, a water-miscible organic solvent is one which is totally or partially miscible with water to the extent defined above, whereas a waterimmiscible organic solvent is one whose partial miscibility at 20° C. is less than 0.5 g, preferably less than 0.1 g and more preferably less 0.05 g water in 100 ml solvent and less than 0.5 g, preferably less than 0.1 g and more preferably less than 0.05 g solvent in 100 ml water. Examples of water-miscible solvents of the invention are chosen from the group consisting of acetone, DMF, dimethylacetamide, N-methylpyrrolidone, glyme, diglyme, THF and dioxane. Examples of organic solvents of the invention non-miscible with water are aromatic or aliphatic solvents, which may be halogenated or not, e.g. chosen from the group consisting of toluene, xylenes (i.e. the orto-, meta-, para-isomers), benzene, clorobenzene, methylene chloride, hexane, heptane, and cyclohexane.

If, according to a first embodiment of the invention, the first organic solvent according to step i) is an organic solvent non-miscible with water, then optional downstream step ia) will be omitted, and the reaction mixture of step i) will be directly subjected to step ii) where an aqueous phase containing an alkali salt of nateglinide will form, without any previous isolation of the nateglinide methyl ester obtained in step i). In particular, according to the first embodiment, the first organic solvent to be used in step i) can be selected from the group consisting of aromatic and aliphatic solvents, which may be halogen-substituted or not, but are always non-miscible with water. E.g., preferred first organic solvents which are non-miscible with water are chosen from the group consisting of toluene, xylenes, benzene, clorobenzene, methylene chloride, hexane, heptane and cyclohexane. The most preferred first organic solvent non-miscible with water is toluene. The amount of first organic solvent non-miscible with water in step i) is preferably comprised between 3 and 20 volumes, as compared to the weight of the trans 4-isopropylcyclohexancarboxylic acid (i.e. ml of solvent per g of acid).

On the other hand, according to a second embodiment of the invention, the first organic solvent to be used in step i) can be selected from the group of water-miscible organic solvents, in particular from the group consisting of acetone, DMF, dimethylacetamide, N-methylpyrrolidone, glyme, diglyme, THF and dioxane.

The preferred water-miscible organic solvent to be employed in step i) as a first solvent of the second embodiment of the invention is acetone. The amount of first organic solvent miscible with water employed in step i) is preferably comprised between 5 and 15 volumes, as compared to the weight of the trans 4-isopropylcyclohexancarboxylic acid (i.e. ml of solvent per g of acid). Preferably, in connection with the second embodiment of the present invention, 10 ml of water-miscible solvent per g trans 4-isopropylcyclohexancarboxylic acid are employed in step i). Always according to the second embodiment of the invention, after using a first water-miscible organic solvent in step i), step ia) is carried out adding water to the reaction mixture of step i), thus precipitating the nateglinide methyl ester formed in step i). The precipitate is washed with water and dried, where after it is dissolved in a second organic solvent which is non-miscible with water. Suitable second organic solvents non-miscible with water to be employed in step ia) are the same as those employed in step i) according to the first embodiment of the process of the present invention, i.e. they can be selected from the group consisting of aromatic and aliphatic solvents, which may be halogen-substituted or not, but are always non-miscible with water. E.g., preferred second organic solvents to be employed in step ia) are chosen from the group consisting of toluene, xylenes, benzene, clorobenzene, methylene chloride, hexane, heptane and cyclohexane. The most preferred second organic solvent non-miscible with water is toluene. The amount of second organic solvent non-miscible with water in step ia) is preferably between 2 and 10 volumes, as compared to the weight of the nateglinide methyl ester (i.e. ml of solvent per g methyl ester). Preferably, in connection with the second embodiment of the present invention, 5 ml solvent organic of solvent non-miscible with water per g nateglinide methyl ester are employed in step ia).

As an acyl chloride in step i) of the present process, preferred is an acyl chloride selected, e.g. from the group consisting of pivaloyl chloride and alkyl- or arylchloroformiates. Particularly preferred are pivaloyl chloride and ethyl chloroformate. More particularly preferred is pivaloyl chloride.

In step i), also carbonyl diimidazole may be employed, though it is less preferred.

When a D-phenylalanine methyl ester salt is used in step i) of the present process, it is preferably the D-phenylalanine methyl ester hydrochloride.

According to a particular embodiment of the present invention, the addition of water and alkali hydroxide in step ii) is carried out in the presence of a phase transfer catalyst, preferably in the presence of tri-caprylmethylammonium chloride.

The alkali hydroxides in step ii) are selected from lithium hydroxide, potassium hydroxide and sodium hydroxide. Potassium hydroxide is preferred.

Optionally, in connection with the first embodiment of the invention, the reaction mixture obtained in step i) may be washed with deionized water, or with a 5% solution of alkali carbonate, before step ii) is carried out.

The hydrochloric acid in step iii) is typically added to the aqueous phase coming from step ii) until a pH comprised between 2.0 and 3.0 is reached.

The present invention also allows providing a process for the preparation of nateglinide in B-form substantially free from H-form, starting from nateglinide not being in the pure B-form e.g. being in B-form contaminated with nateglinide in H-form in different amounts (or starting from any other known polymorph of natgelinide or from mixtures thereof), the said process comprising dissolving nateglinide in water with alkali hydroxide to obtain an aqueous solution of alkali salt of nateglinide, and adding thereto hydrochloric acid at room temperature, preferably in the temperature range from 5° C. to 20° C., more preferably from 10° C. to 20° C. and still more preferably from 15° C. to 20° C., such that nateglinide in the pure B-form precipitates therefrom. According to the present process, the hydrochloric acid is added to the aqueous solution of nateglinide alkali salt until a pH comprised between 2.0 and 3.0 is obtained.

The present process fulfils the requirements of industrial scalability, and shows the following remarkable advantages over the prior art processes: the yields are very high (higher than 90% in the preferred embodiments), the preferred reactants bringing about the condensation step between the two precursors are cheap, and the final product obtained is completely free from by-products, such as the above said dimeric form IPP or the nateglinide methyl ester. Preferably, namely if the precipitation in step iii) is carried out at room temperature, preferably in the temperature range from 5° C. to 20° C., more preferably from 10° C. to 20° C. and still more preferably from 15° C. to 20° C., the final nateglinde obtained is in the pure B-form, substantially free from nateglinide crystals of the H-form. Accordingly, unlike in the prior art where a yield-reducing final work-up was imperative, no re-crystallization of the product obtained by the method of the present invention is necessary to impart the same pharmaceutically acceptable grade. Indeed, the product provided by the present invention is characterized by a high purity, under both, the chemical and possibly the polymorphic aspect. The chemical purity of the product has been established through HPLC methods. On the other hand, the grade of polymorphic purity of the product obtained by the present process has been evaluated by DSC analysis, obtaining curves showing an only peak specific for the B-form of nateglinide. These results have been confirmed IR-spectrometrically and through X-ray powder diffraction analysis.

The following examples are reported to give a non-limiting illustration of the present invention.

EXAMPLE 1

Preparation of D-phenylalanine methyl ester hydrochloride.

66.0 g (0.40 mol) of D-phenylalanine were suspended at room temperature in 400 ml of methanol in an anhydrous flask. The thus obtained white suspension was cooled to a temperature of 0±5° C., and then 56.0 ml of tionyl chloride were added drop wise in about 2 hours, maintaining the temperature in the range 0±5° C.

The temperature of the suspension thus obtained was brought up to 40±5° C., and maintained for 6 hours, then returned to room temperature.

The reaction mixture was stirred overnight at room temperature, and then concentrated under vacuum so as to remove most of the solvent; the residue was dissolved in 200 ml of toluene, and the thus obtained solution was concentrated under vacuum once more, until a residue able to be stirred was obtained.

To this residue 400 ml of acetone were added, and the thus obtained suspension was cooled to a temperature of 0±5° C. for 2 hours.

A solid product was formed, which is filtered and washed with acetone (2×50 ml), thus obtaining 83.34 g of wet white product, corresponding to 81.09 g of dry D-phenylalanine methyl ester hydrochloride (yield=94.1%).

EXAMPLE 2

Preparation of nateglinide according to the first embodiment of the invention (i.e. carrying out step i) in an organic solvent non-miscible with water and omitting optional step ia)).

15.0 g (0.0881 mol) of trans 4-isopropylcyclohexancarboxylic acid were put into an anhydrous flask under nitrogen atmosphere together with 225 ml of toluene. Under stirring 10.9 g (0.108 mol) of triethylamine were then added, thus obtaining a thick suspension, which was cooled to 0±5° C. while maintaining under stirring.

To this suspension 11.7 g (0.0969 mol) of pivaloyl chloride were added drop wise, maintaining temperature in the range 0±5° C. The reaction mixture was made to react for 30 minutes at 0±5° C., and then temperature is brought up to 20±5° C. and maintained for 2 hours.

10.9 g (0.108 mol) of triethylamine, and then 19.05 g (0.0881 mol) of D-phenylalanine methyl ester hydrochloride prepared as described above in Example 1 were added to the reaction mixture portion wise in 30 minutes, which was then made to react at 20±5° C. for 18 hours.

Temperature was brought up to 75±5° C. and, maintaining temperature in this range, 2 washings with a 5% aqueous solution of sodium carbonate (2×175 ml) are carried out. The organic phases were merged and added with 225 ml of deionised water, 13.5 g of 30% solution of sodium hydroxide and a drop of Aliquat. The reaction mixture was stirred at 50±5° C. for 5 hours.

Once reaction was completed, the aqueous phase was separated, added with 0.1 g of carbon LSM and filtered on a dicalite panel. The thus obtained filtrate was put in a flask and at temperature of 35/40° C. HCl 10% was added until pH 2.5±0.5.

The suspension is cooled to 25°-30° C., maintained at this temperature for 1 hour, and then filtered and washed with deionised water until complete disappearance of chlorides. 62.1 g of wet product and 25.45 g of dry product were obtained (yield=91.0%). A DSC analysis has been carried out on the dry product, revealing that a mixture of B-form and H-form had been obtained. The product was however of high chemical purity according to HPLC analysis. The product may thus be converted into the desired pure polymorphic form through methods described herein or known in the art.

EXAMPLE 3

Preparation of nateglinide according to the first embodiment of the invention (i.e. carrying out step i) in an organic solvent non-miscible with water and omitting optional step ia)).

The procedure described above in Example 1 was repeated with the same reagents and under the same operative conditions, but diminishing the amount of toluene, from 225 to 150 ml, thus obtaining 24.2 g of dry end-product (yield=86.6%). A DSC analysis has been carried out on the dry product, revealing that a mixture of B-form and H-form had been obtained. The product was however of high chemical purity according to HPLC analysis. The product may thus be converted into the desired pure polymorphic form through methods described herein or known in the art.

EXAMPLE 4

Preparation of nateglinide according to the first embodiment of the invention (i.e. carrying out step i) in an organic solvent non-miscible with water and omitting optional step ia)).

The procedure described above in Example 1 was repeated under the same operative conditions and with the same reagents, except the pivaloyl chloride, which was replaced by ethylchloroformiate, thus obtaining 20.8 g of dry end-product (yield=74.4%). A DSC analysis has been carried out on the dry product, revealing that a mixture of B-form and H-form had been obtained. The product was however of high chemical purity according to HPLC analysis. The product may thus be converted into the desired pure polymorphic form through methods described herein or known in the art.

EXAMPLE 5

Preparation of nateglinide in B-form according to the second embodiment of the invention (i.e. carrying out step i) in a first organic solvent miscible with water and carrying out step ia) under dissolution in a second organic solvent non-miscible with water).

A 1l-flask, at room temperature, under nitrogen and equipped with internal thermometer, stirrer and dropping funnel, was charged with trans-4-isopropylcyclohexylcarboxylic acid (30 g, 0.1762 mol) and 300 ml acetone. Upon total dissolution of the acid, triethylammine (21.8 g, 0.2152 mol) was added (no change of temperature was observed). The solution thus obtained was then cooled to 5±5° C. and pivaloyl chloride (23.4 g, 0.1938 mol) was added dropwise within 30 minutes and without exceeding the temperature interval. Due to the precipitation of triethylammine hydrochloride, a suspension was obtained. Once the addition was completed, the temperature was kept at 5±5° C. for 30 minutes, whereafter it was left standing until room temperature (20°±5° C.) was reached (about three hours). At this point, a second charging with triethylammine (21.8 g, 0.2152 mol) was made and D-phenylalanine methyl ester hydrochloride (38.1 g, 0.1762 mol) was added in small amounts, avoiding excessive exothermic heating up of the reaction mixture (some initial exothermic heating was due to the setting free of base). The mixture thus obtained thickened considerably due to the formation of another equivalent of triethylamine hydrochloride. The reaction mixture was left standing at room temperature (20°±5° C.) overnight.

The next morning, a quantitative TLC was conducted such as to trace down eventual traces of residual, non-reacted phenyl alanine methyl ester (not detectable). The suspension was thick but could still be stirred. The product thus obtained was then precipitated through the addition of 300 ml of deionized water to the suspension. The suspension was then cooled for at least two hours to 0°±5° C., filtered and washed three times with 50 ml of deionized water, 73.0 g of wet product, corresponding to 52.6 g of the dry, white intermediate (nateglinide methyl ester) were obtained (theoretical yield: 58.4 g, effective yield: 90.07%).

Next, a 2 l-flask was charged at room temperature with 52.0 g nateglinide methyl ester, 260 ml toluene, 520 ml deionized water, one drop of Aliquat® 336 (tricaprylmethyl ammonium chloride) and 35.2 g of aqueous potassium hydroxide (50% by weight solution). Under vigorous stirring, the content of the flask was heated up to 45°-50° C. (the two phases were still clear); after 5 hours, hydrolysis of the methyl ester was completed. The two phases were thus separated at 50° C. and the toluene (on top) was discarded, whereas 1.0 g of carbon LSM was added to the aqueous phase which was then filtered through a dicalite panel. The thus obtained clear and colourless solution was then cooled to 15°-20° C. Nateglinide was then precipitated from the solution through the addition of 120 ml aqueous HCl (10%), such as to impart a pH of 2.5±0.5 carefully controlling the temperature interval of 15° C. to 20° C. and without exceeding the same. After the precipitation, the product was filtered and washed until disappearance of chlorides. 94.0 g wet product equivalent 48.3 g dry product, natgelinide B-form was obtained (theoretical yield: 49.8 g; effective yield 97%). A DSC analysis has been carried out on the dry product obtaining the peak specific of the nateglinide in B-form (128.97° C.).

EXAMPLE 6

Preparation of nateglinide according to the first embodiment of the invention (i.e. carrying out step i) in an organic solvent non-miscible with water and omitting optional step ia)).

A 500 ml flask was charged, under nitrogen, at room temperature with 150 ml toluene, 15.7 g 1,1-carbonyldiimidazole, and 15.0 g trans-4-isopropylcyclohexylcarboxylic acid. The mixture thus obtained was heated to 45±5° C., where after the same was left cooling down to room temperature (20±5° C.) and 15 ml triethyl ammine was charged. Thereafter 19.05 g D-phenylalanine methyl ester hydrochloride was added in small amounts. After completion of the addition, the mixture was heated to reflux (108° C.) and maintained at reflux for 16 hours. A TLC control reavaels that the D-phenylalanine methyl ester still unreacted is less than 2%. Thereafter, reaction mixture was cooled to 70±5° and washed three times with 100 ml deionized water. To the washed organic solution, 150 ml deionized water, 23.5 g 30% NaOH and 1 drop of Aliquat® phase transfer catalyst were added. The biphasic mixture thus obtained was heated for 4 hours to 45±5° C. Thereafter, the phases were separated at 70±5° C. and the aqueous phase was diluted with 75 ml of deionized water, 0.3 g of carbon LSM was added and filtration on a decalite panel was carried out. The nateglinide was then precipitated, at 45° C. trough addition of 10% aqueous HCl solution until a pH of 2.5±5 was reached. The precipitate was washed at rt (20° C.) and washed with water until disappearance of chlorides. 22.7 g of dried product were obtained, corresponding (compared to 27.96 g of theoretical yield) to an effective yield of 81.2%. The product thus obtained was tested through DSC analysis, revealing that a mixture of B-form and H-form had been obtained. The product was however of high purity according to HPLC analysis. The product may thus be converted into the desired pure polymorphic form through methods described herein or known in the art.

EXAMPLE 7

Preparation of nateglinide according to the first embodiment of the invention (i.e. carrying out step i) in an organic solvent non-miscible with water and omitting optional step ia)).

Example has been carried out exactly as example 6 above, except for the fact that the condensation of the imidazolide derived from the acid with D-phenylalanine methyl ester hydrochloride was conducted at 40°-45° C. for 36 hours (c.f. above where 16 hours at reflux were applied). Likewise, with these modified conditions, a residual amount of unreacted 2% D-phenyl alanine methyl ester (checked through TLC) was reached. After working up as above, an effective yield of 85.83% was reached. The product thus obtained was tested through DSC analysis, revealing that a mixture of B-form and H-form had been obtained. The product was however of high purity according to HPLC analysis. The product may thus be converted into the desired pure polymorphic form through methods described herein or known in the art.

EXAMPLE 8

Preparation of nateglinide in B-form according to the second embodiment of the invention (i.e. carrying out step i) in a first organic solvent miscible with water and carrying out step ia) under dissolution in a second organic solvent non-miscible with water).

A 1 l-flask, at room temperature, under nitrogen and equipped with internal thermometer, stirrer and dropping funnel, was charged with trans-4-isopropylcyclohexylcarboxylic acid (30 g, 0.1762 mol) and 300 ml acetone. Upon total dissolution of the acid, triethylamine (21.8 g, 0.2152 mol) was added (no change of temperature was observed). The solution thus obtained was then cooled to 0±5° C. and ethyl cloroformiate (18.6 ml, 0.1938 mol) was added dropwise within 30 minutes and without exceeding the temperature interval. Once the addition was completed, the mixture was left standing until room temperature (20°±5° C.) was reached and stirred for about three hours. At this point, a second charging with triethylammine (21.8 g, 0.2152 mol) was made and D-phenylalanine methyl ester hydrochloride (38.1 g, 0.1762 mol) was added in small amounts, avoiding excessive exothermic heating up of the reaction mixture (some initial exothermic heating was due to the setting free of base). The mixture thus obtained thickened considerably due to the formation of another equivalent of triethylamine hydrochloride. The reaction mixture was left stirring at 25°±5° C. overnight.

The next morning, a quantitative TLC was conducted such as to trace down eventual traces of residual, non-reacted phenyl alanine methyl ester (less than 2%—note that this value, unlike in the case of the use of pivaloyl chloride reported in example 5 above—remains the same even, if the reaction time is extended well beyond the value reported here). The suspension was thick but could still be stirred. The product thus obtained was then precipitated through the addition of 300 ml of deionized water to the suspension. The suspension was then cooled for at least two hours to 0°±5° C., filtered and washed three times with 50 ml of deionized water, 66.0 g of wet product, corresponding to 45.8 g of the dry, white intermediate (nateglinide methyl ester) were obtained (theoretical yield: 58.4 g, effective yield: 78.42%).

Next, a 2 l-flask was charged at room temperature with 45.8 g nateglinide methyl ester, 230 ml toluene, 520 ml deionized water, one drop of Aliquat® 336 (tricaprylmethyl ammonium chloride) and 35.2 g of aqueous potassium hydroxide (50% by weight solution). Under vigorous stirring, the content of the flask was heated up to 45°-50° C. (the two phases were still clear); after 5 hours, hydrolysis of the methyl ester was completed. The two phases were thus separated at 50° C. and the toluene (on top) was discarded, whereas 1.0 g of carbon LSM was added to the aqueous phase which was then filtered through a dicalite panel. The thus obtained clear and colourless solution was then cooled to 15°-20° C. Nateglinide was then precipitated from the solution through the addition of 120 ml aqueous HCl (10%), such as to impart a pH of 2.5±0.5 carefully controlling the temperature interval of 15° C. to 20° C. and without exceeding the same. After the precipitation, the product was filtered and washed until disappearance of chlorides. After drying of the wet product equivalent 43.25 g dry product, natgelinide B-form was obtained corresponding to an effective yield of 98.6% for the sole hydrolysis step. A DSC analysis has been carried out on the dry product obtaining the peak specific of the nateglinide in B-form (130.44° C.).

EXAMPLE 9

HPLC Purity Testing.

Figure 4:
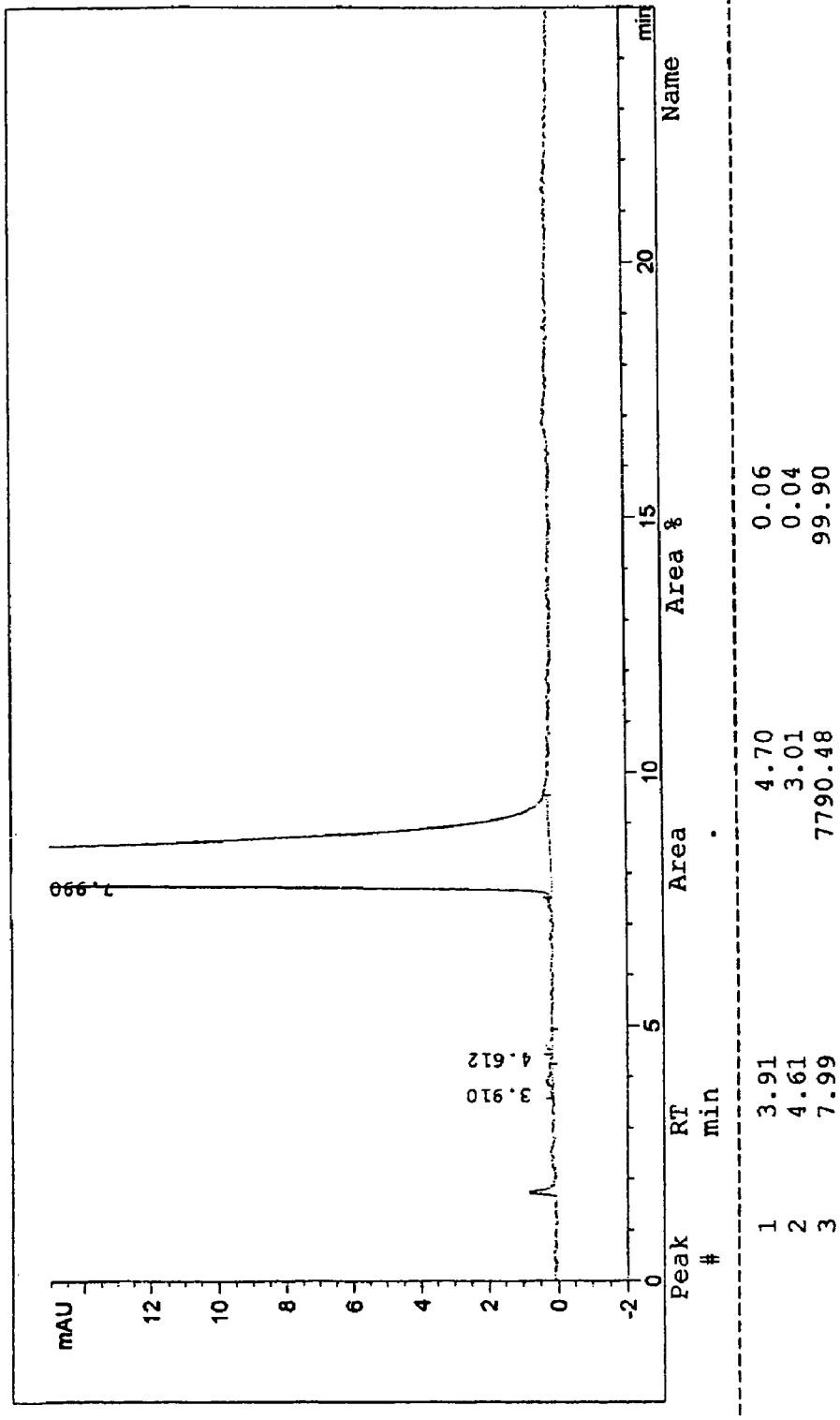
Figure 5:
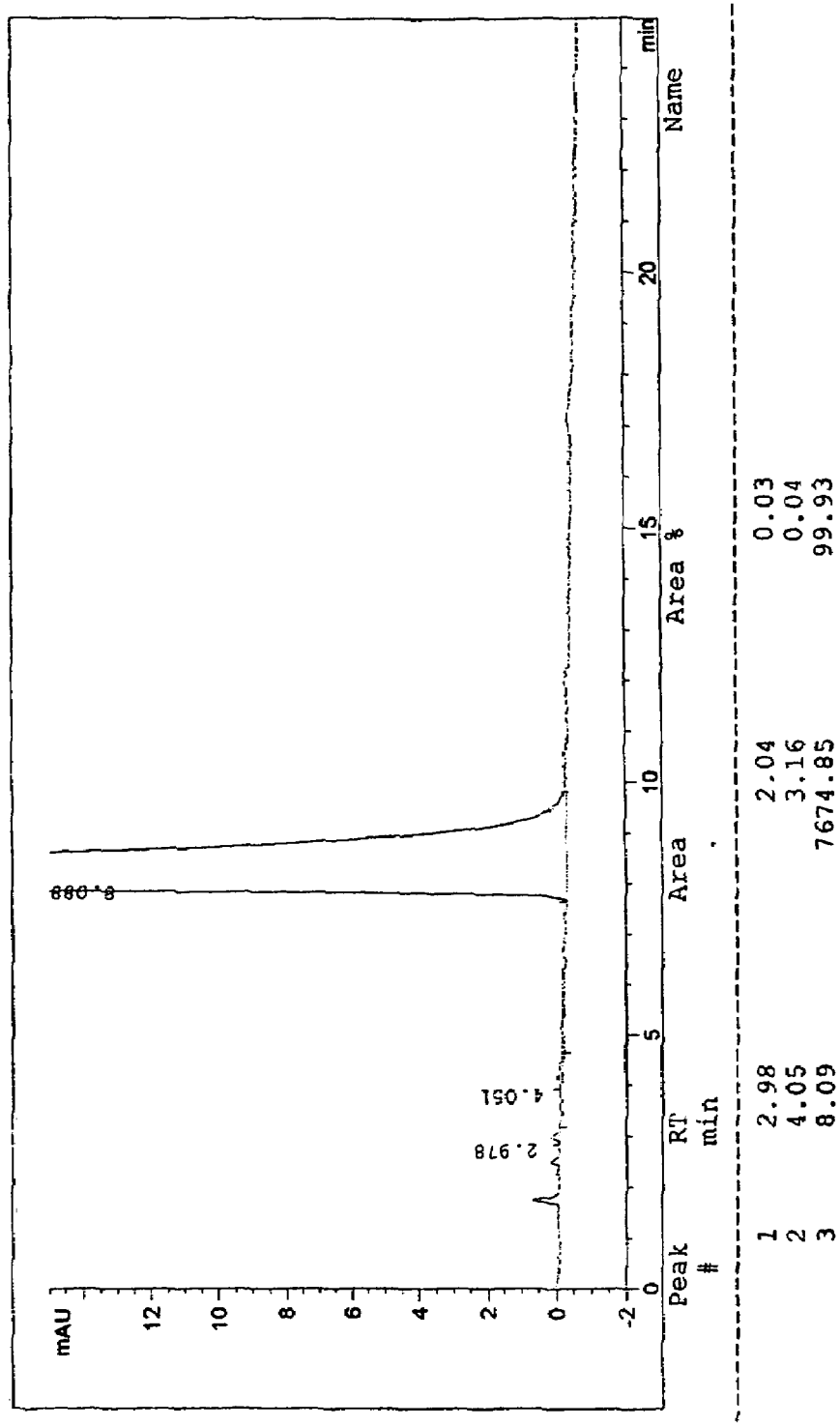
Figure 6:
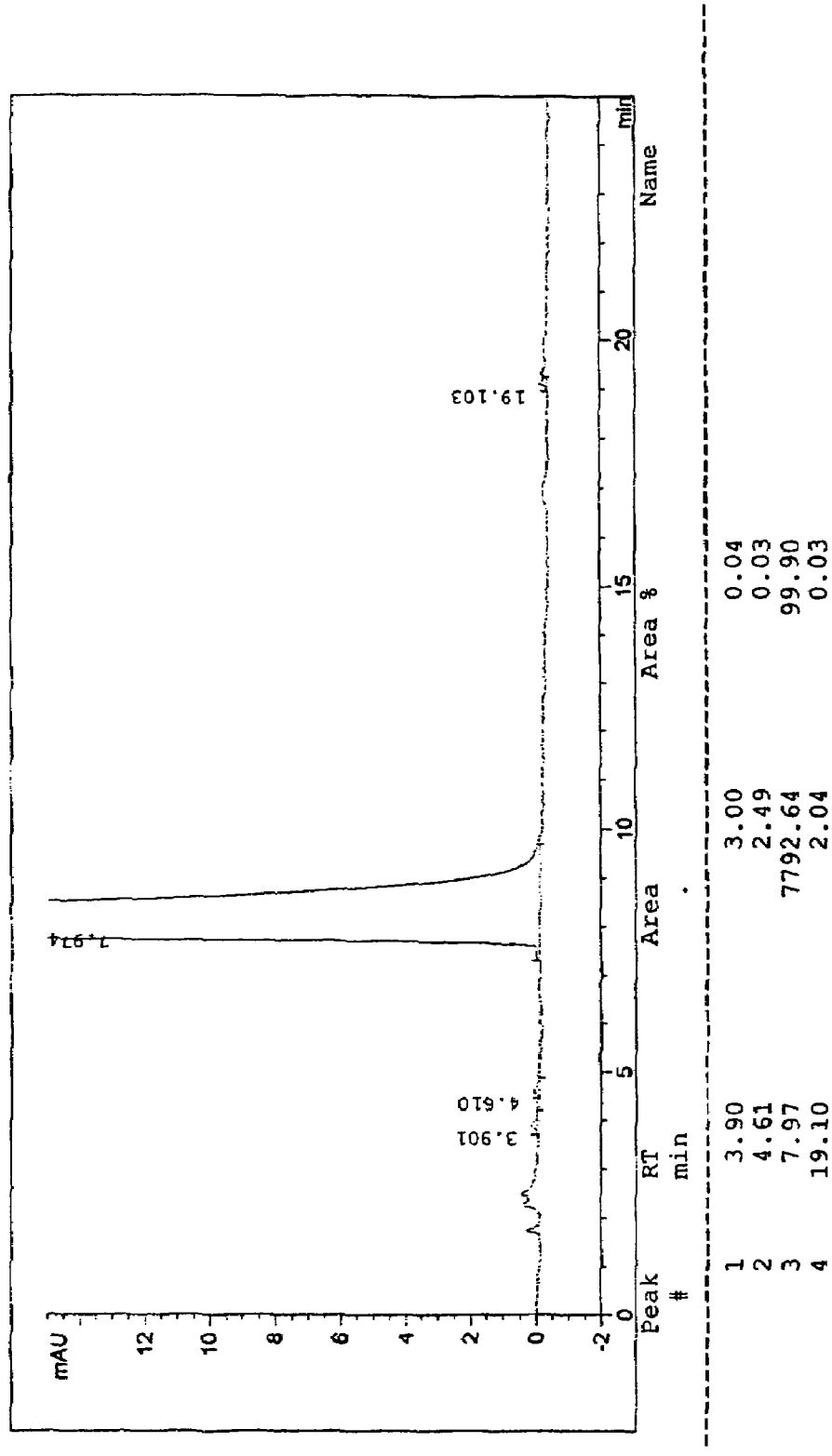

The chemical purity of the nateglinide obtained according to example 5 was evaluated on a HPLC equipped with a sperisorb ODS-1 250×4.6 mm column and an UV-detector with acetonitrile—1 g/l phosphoric acid as liquid phase. Previously, comparative chromatograms of nateglinide methyl ester (FIG. 1), phenylalanine methyl ester hydrochloride (FIG. 2), and of phenylalanine, nateglinide, phenylalanine methyl ester, and nateglinide methyl ester together (FIG. 3) were recorded to establish the respective retention times. It therefore appears that the three samples of nateglinide obtained with the process according to the present invention (FIGS. 4, 5 and 6 respectively) display a HPLC purity≧99.9%.

EXAMPLE 10

Precipitation of the pure B-form at various temperatures and at various concentrations.

Different crops of pure B-form of nateglinide were obtained, after repeating the synthesis set out in example 5, from different portions of mother liquor applying different thermic conditions both, at standard conditions and after diluting the aqueous phase of stepii) twice with water before carrying out the precipitation according to step iii).

Figure 7:
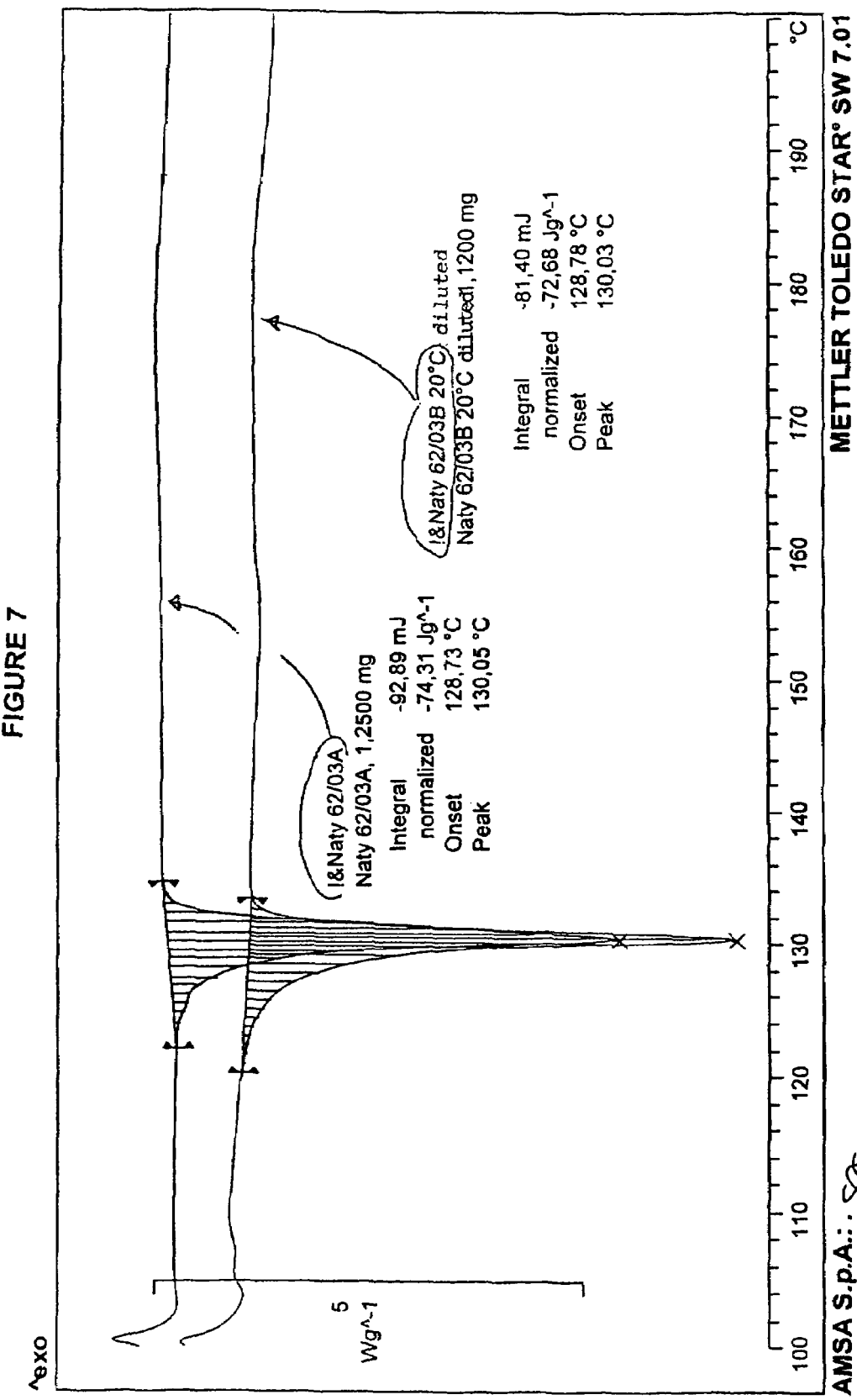

In particular, FIG. 7 shows the DSC analysis of two samples from the same batch, wherein the upper curve (termed Naty 62/03A) shows the DSC of a sample precipitated at 20° C. from the mother liquor (the dilution employed being the one of example 5 above), recorded on DSC822 Mettler Toledo equipment actuating a heating rate of 10° C./min between 100° C. and 200° C. (1.25 mg having been employed for the registration of the curve and the data of the curve plotted by the equipment being as follows: Integral: −92.89 mJ; normalized: −74.31 J/g; onset: 128.73° C.; Peak 130.05° C.). Always in FIG. 7, the lower curve (termed Naty 62/03B) shows the DSC of a sample precipitated at 20° C. from the mother liquor (the dilution employed being twice the one of example 5 above), recorded on DSC822 Mettler Toledo equipment actuating a heating rate of 10° C./min between 100° C. and 200° C. (1.12 mg having been employed for the registration of the curve and the data of the curve plotted by the equipment being as follows: Integral: −81.40 mJ; normalized: −72.68 J/g; onset: 128.78° C.; Peak 130.03° C.).

Figure 8:
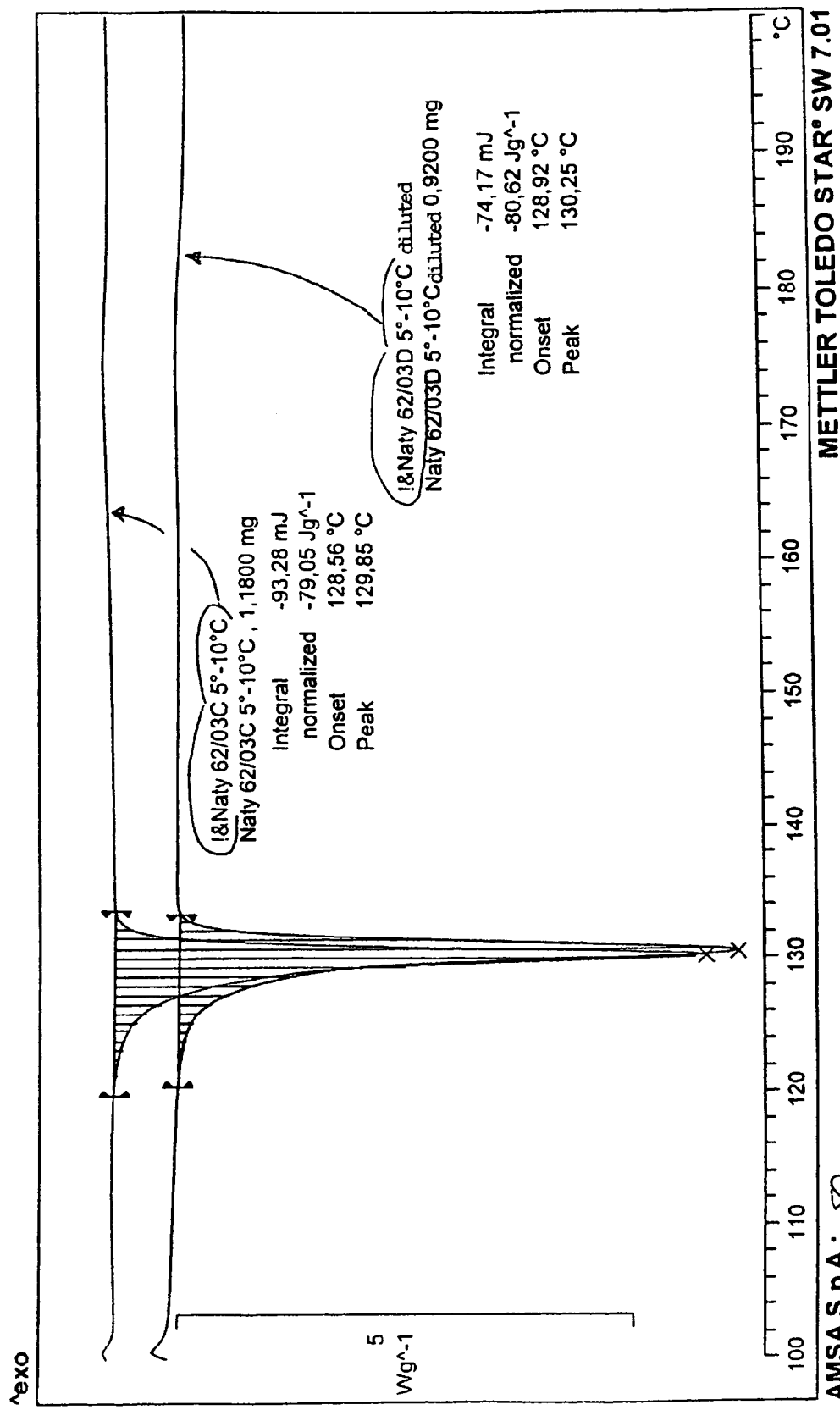

Further, FIG. 8 shows the DSC analysis of two samples from the same batch, wherein the upper curve (termed Naty 62/03C) shows the DSC of a sample precipitated at 5-10° C. from the mother liquor (the dilution employed being the one of example 5 above), recorded on DSC822 Mettler Toledo equipment actuating a heating rate of 10° C./min between 100° C. and 200° C. (1.18 mg having been employed for the registration of the curve and the data of the curve plotted by the equipment being as follows: Integral: −93.28 mJ; normalized: −79.05 J/g; onset: 128.56.C; Peak 129.85° C.). Always in FIG. 8, the lower curve (termed Naty 62/03D) shows the DSC of a sample precipitated at 5-10° C. from the mother liquor (the dilution employed being twice the one of example 5 above), recorded on DSC822 Mettler Toledo equipment actuating a heating rate of 10° C./min between 100° C. and 200° C. (0.92 mg having been employed for the registration of the curve and the data of the curve plotted by the equipment being as follows: Integral: −74.17 mJ; normalized: −80.62 J/g; onset: 128.92° C.; Peak 130.25° C.).

Figure 9:
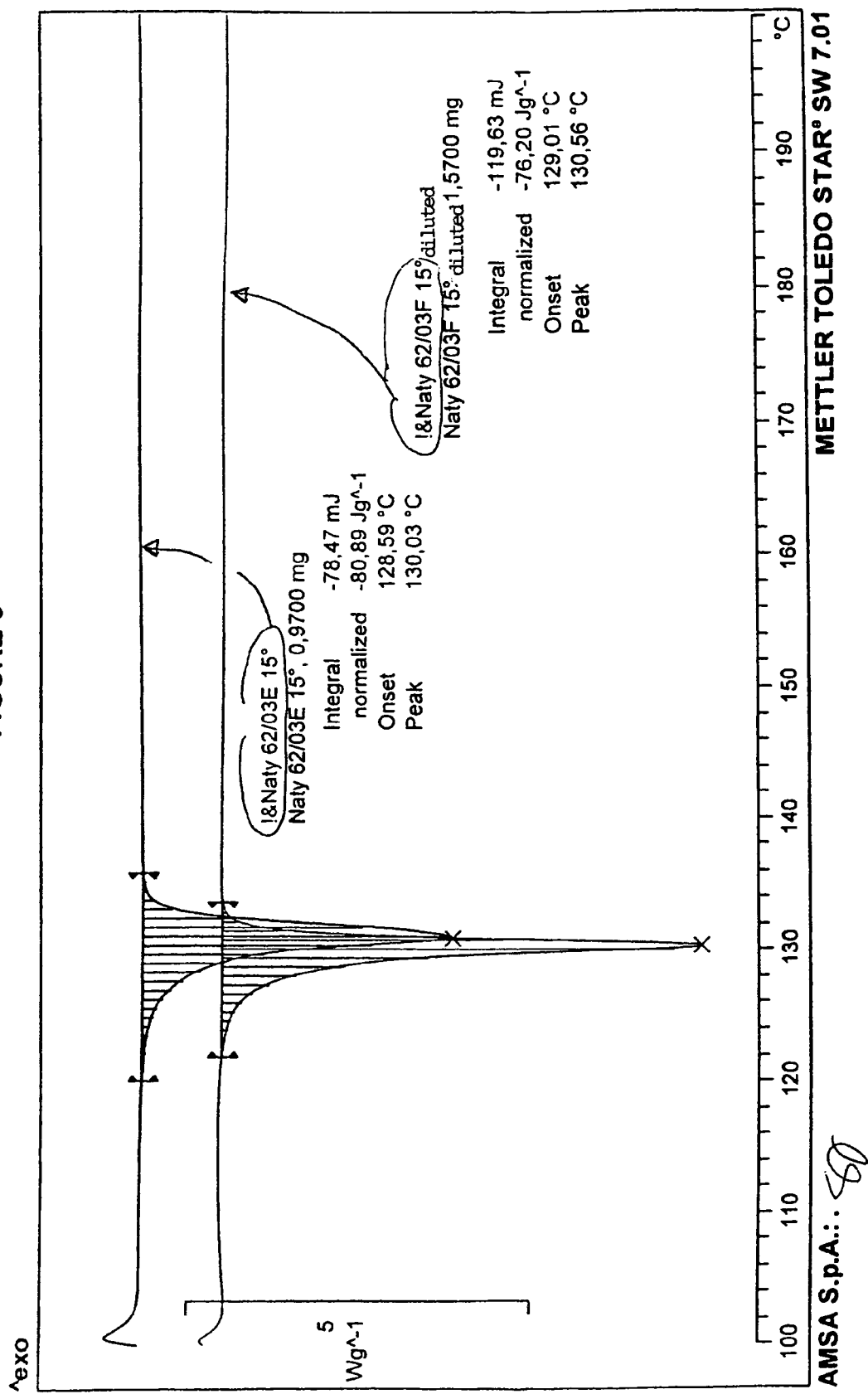

Further, FIG. 9 shows the DSC analysis of two samples from the same batch, wherein the upper curve (termed Naty 63/03E) shows the DSC of a sample precipitated at 15° C. from the mother liquor (the dilution employed being the one of example 5 above), recorded on DSC822 Mettler Toledo equipment actuating a heating rate of 10° C./min between 100° C. and 200° C. (0.97 mg having been employed for the registration of the curve and the data of the curve plotted by the equipment being as follows: Integral: −78.47 mJ; normalized: −80.89 J/g; onset: 128.59.C; Peak 130.03° C.). Always in FIG. 9, the lower curve (termed Naty 62/03F) shows the DSC of a sample precipitated at 15° C. from the mother liquor (the dilution employed being twice the one of example 5 above), recorded on DSC822 Mettler Toledo equipment actuating a heating rate of 10° C./min between 100° C. and 200° C. (1.57 mg having been employed for the registration of the curve and the data of the curve plotted by the equipment being as follows: Integral: −119.63 mJ; normalized: −76.20 J/g; onset: 129.01° C.; Peak 130.56° C.).

Figure 10:
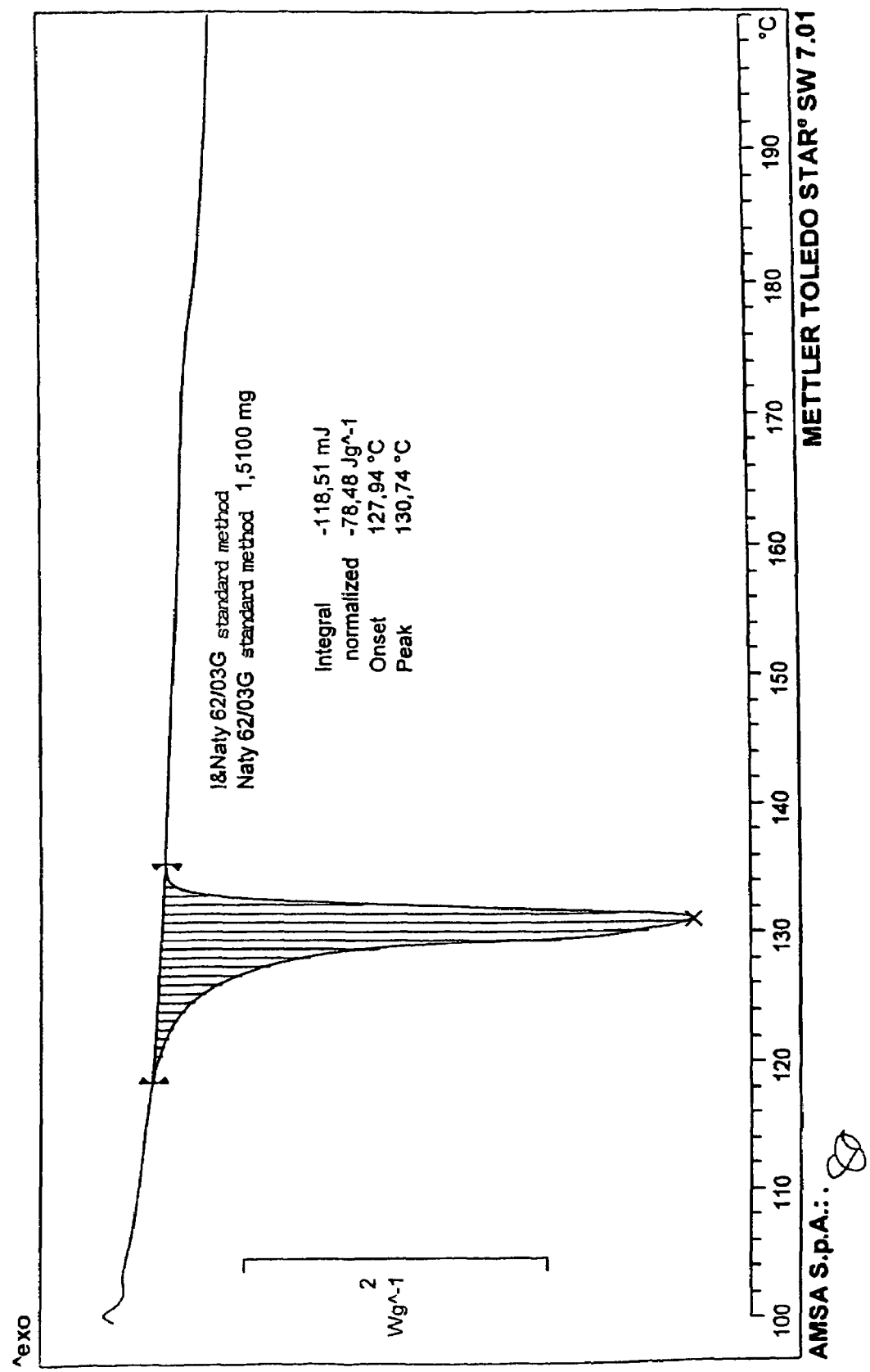

Finally, for confirmation purposes, a second sample, termed Naty 62/03/G, was treated exactly like sample Naty 62/03/A (dilution as in example 5, precipitation at 20° C.), and the respective DSC curve, shown in FIG. 10, was recorded on DSC822 Mettler Toledo equipment actuating a heating rate of 10° C./min between 100° C. and 200° C. (1.5100 mg having been employed for the registration of the curve and the data of the curve plotted by the equipment being as follows: Integral: −118.51 mJ; normalized: −78.48 J/g; onset: 127.94° C.; Peak 130.74° C.).

The DSC curves as reported herein were double-checked through IR analysis, fully confirming the high polymorphic purity of the B-form preparations obtained by the methods of the present invention.

EXAMPLE 11

Registration of X-ray powder diffraction data of the pure B-form obtained with the method of the present invention.

Figure 11:
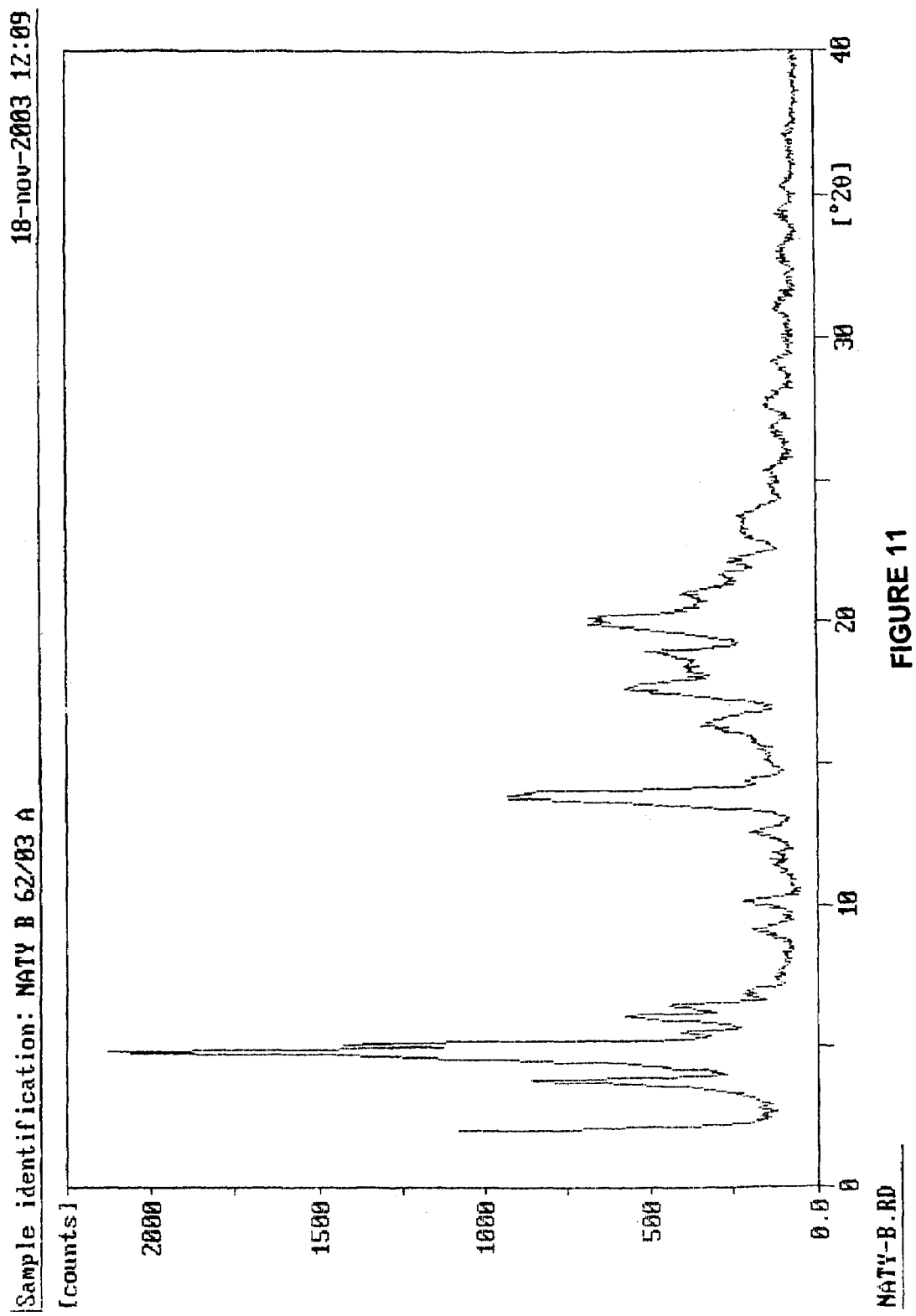

FIG. 11 shows the powder X-ray diffractogram of the sample 62/03A recorded on a Philips diffractometer PW 1710. As it appears from FIG. 11, the X-ray powder diffractogramm corresponds fully to the known one of the B-form shown in EP 526 171 and U.S. Pat. No. 5,488,150, respectively (see FIG. 1 therein). Note that not only the peak positions (two theta), but also the relative peak intensities correspond substantially to the data given in the prior art. In particular, in FIG. 11, there are no diffraction peaks, whose occurrence would be characteristic for the sole H-form of nateglinide, as its powder diffractogram appears from FIG. 3 of EP 526 171 and U.S. Pat. No. 5,488,150, respectively. Hence, it can be concluded that the B-form of nateglinide which may be obtained through the methods provided by the present invention, is substantially free of the H-form.

In particular, the pure B-form obtained through the methods of the present invention is characterized through an X-ray powder diffractogram comprising reflection peaks at 4.8±1° two theta, 5.1±1° two theta, 13.8±1° two theta, 14.0±1° two theta, and 17.7±1° two theta. In the following Appendix 1, there are set out the analytical data recorded by the Philips PW 1710 diffractometer for sample 62/03A and underlying FIG. 11.

Figure 3:
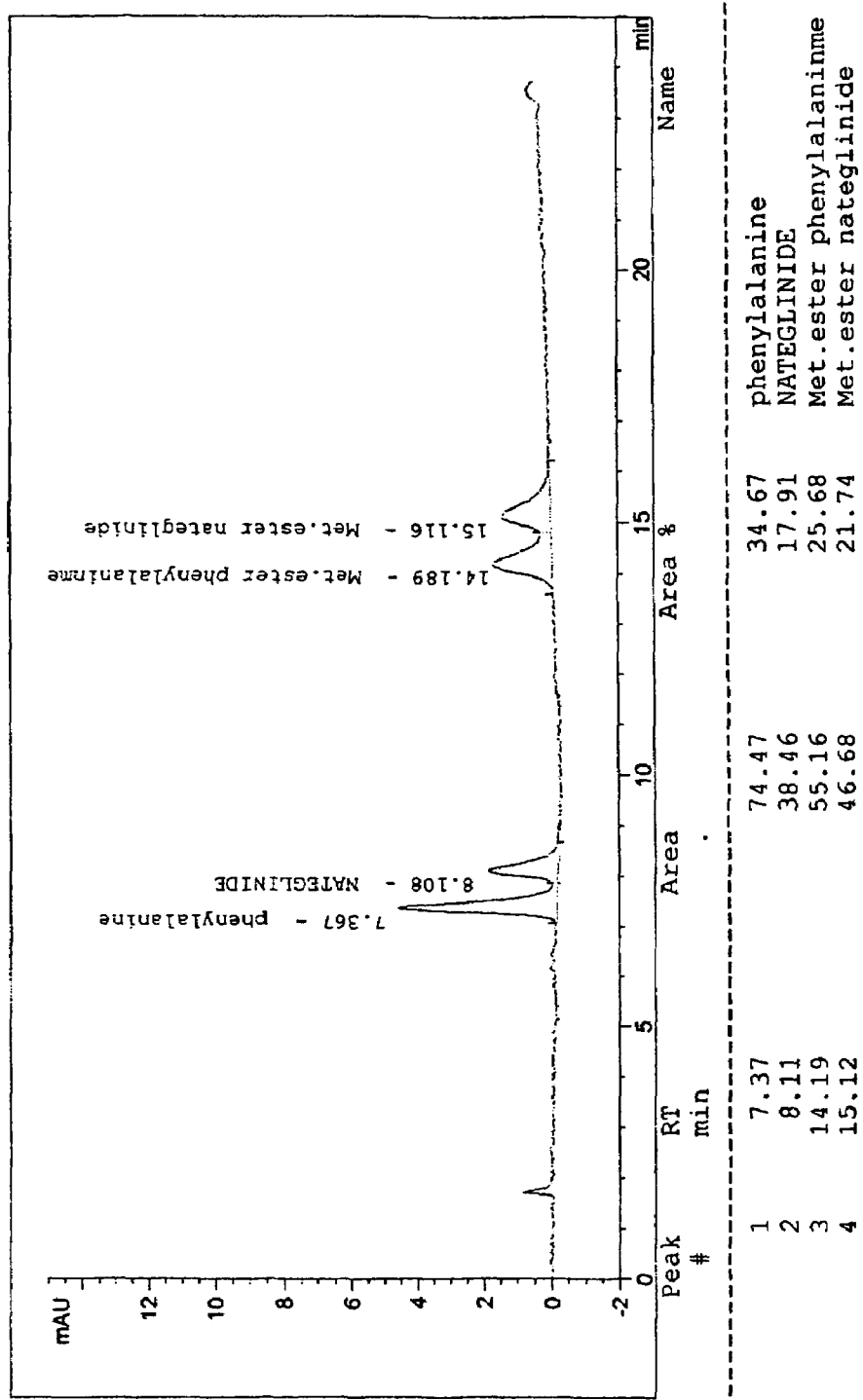
FIG. 3 is a HPLC chromatogram of phenylalanine, nateglinide, phenyl alanine methyl ester and nateglinide methylester, FIGS. 4, 5 and 6, respectively are HPLC chromatograms of nateglinide preparations obtained through the process of the present invention, FIGS. 7, 8, 9 and 10, respectively are DSC curves showing different crops of nateglinide B-form precipitated at different temperatures and at different dilutions from the mother liquor.
Figure 12:
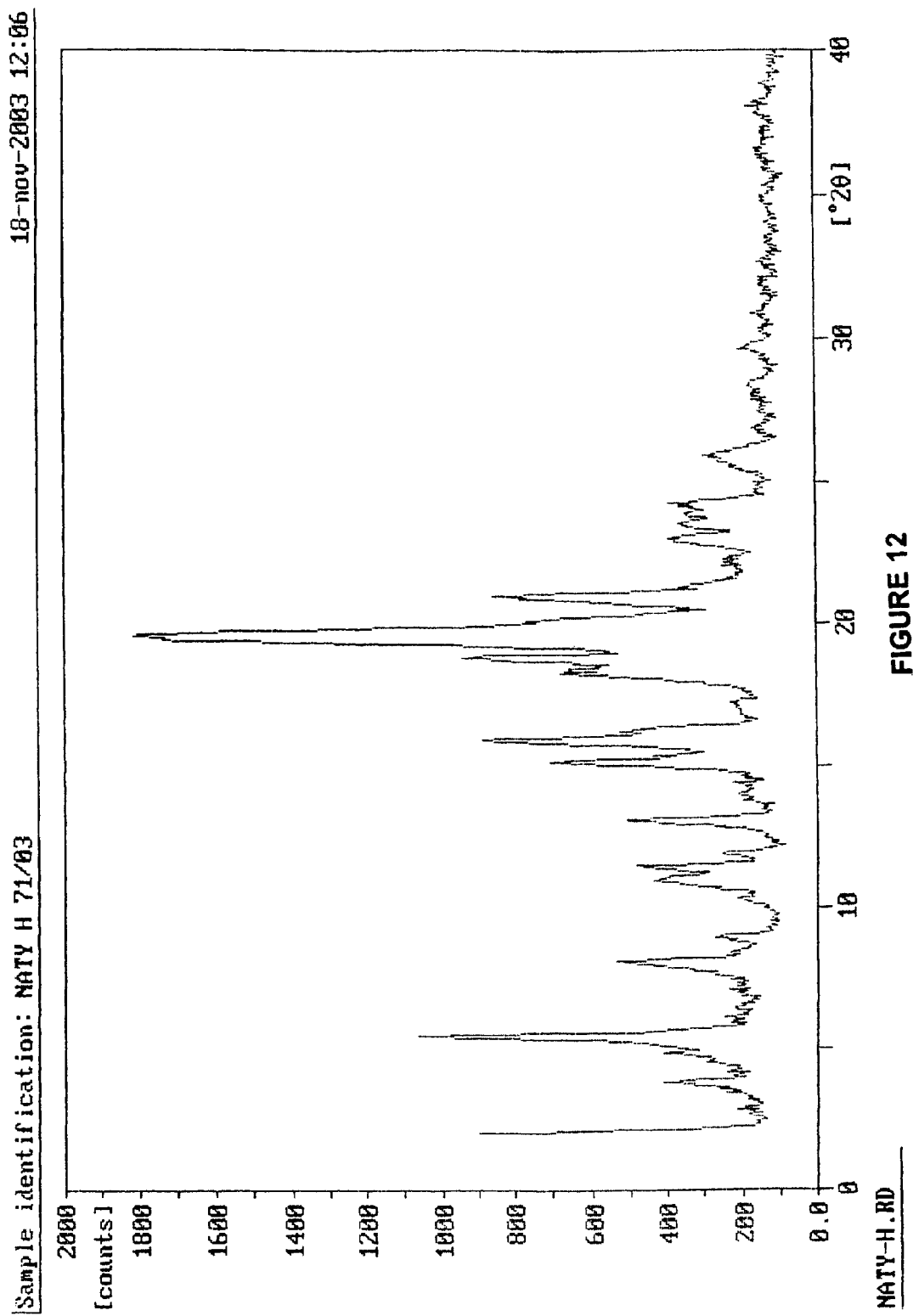
FIGS. 12 and 13 are comparative X-ray powder diffractograms of a sample of nateglinide H-form and of a mixture of B-form and H-form, respectively.

FIG. 12 shows, for comparative purposes, an X-ray powder diffractogram of the pure H-form of nateglinide (sample 71/03) used for the validation and double-checking of the analytical data herein described, from which it can be seen that that the peak positions (two theta) correspond to those of the diffractogram according to FIG. 3 of EP 526 171 and U.S. Pat. No. 5,488,150, respectively. While there are some differences in the relative intensities, these may be attributed to effects brought about by preferred orientations of the crystals.

In the following Appendix 2, there are set out the analytical data recorded by the Philips PW 1710 diffractometer for sample 71/03 and underlying FIG. 12.

Figure 2:
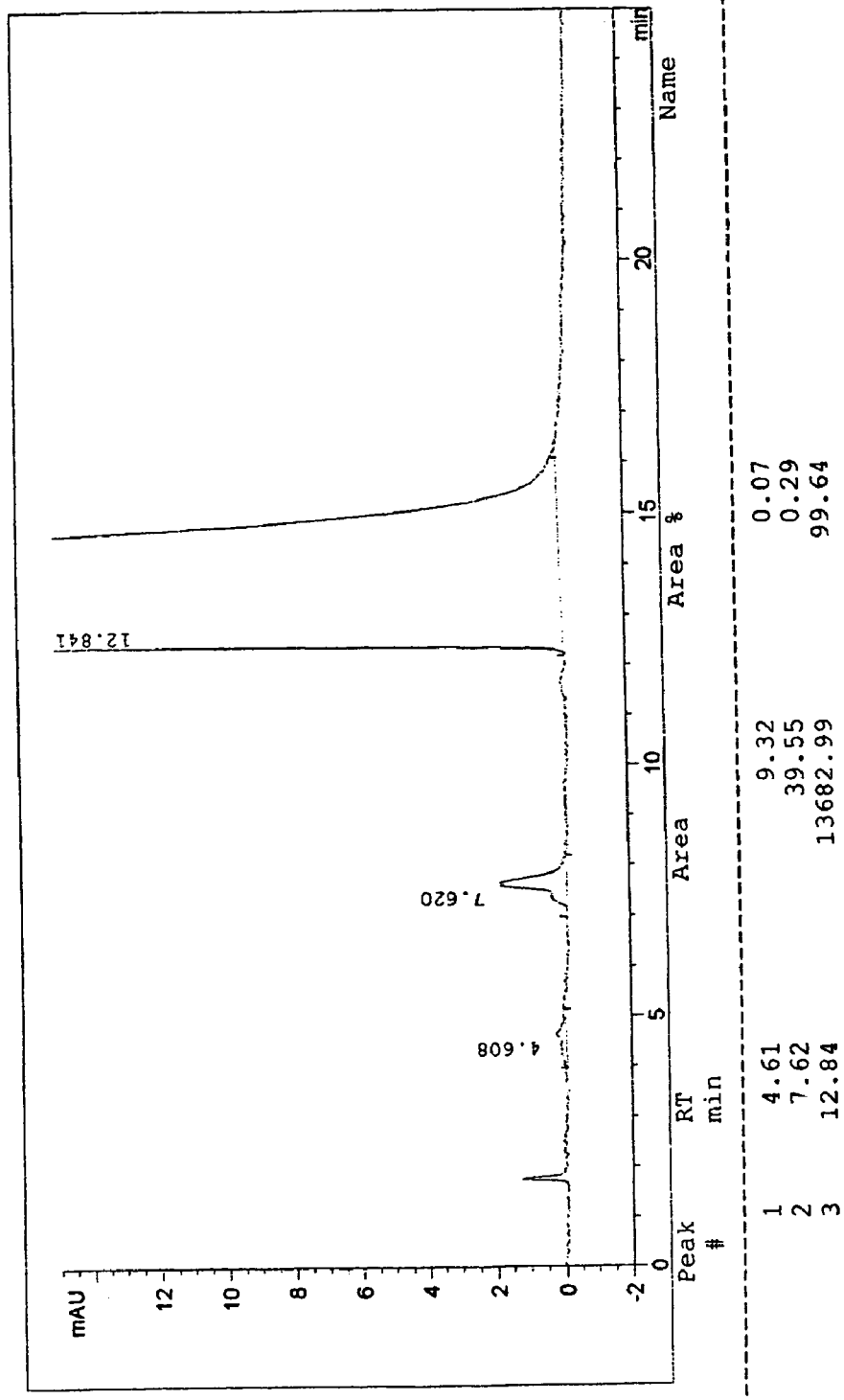
FIG. 2 is a HPLC chromatogram of phenyl alanine methyl ester hydrochloride.
Figure 13:
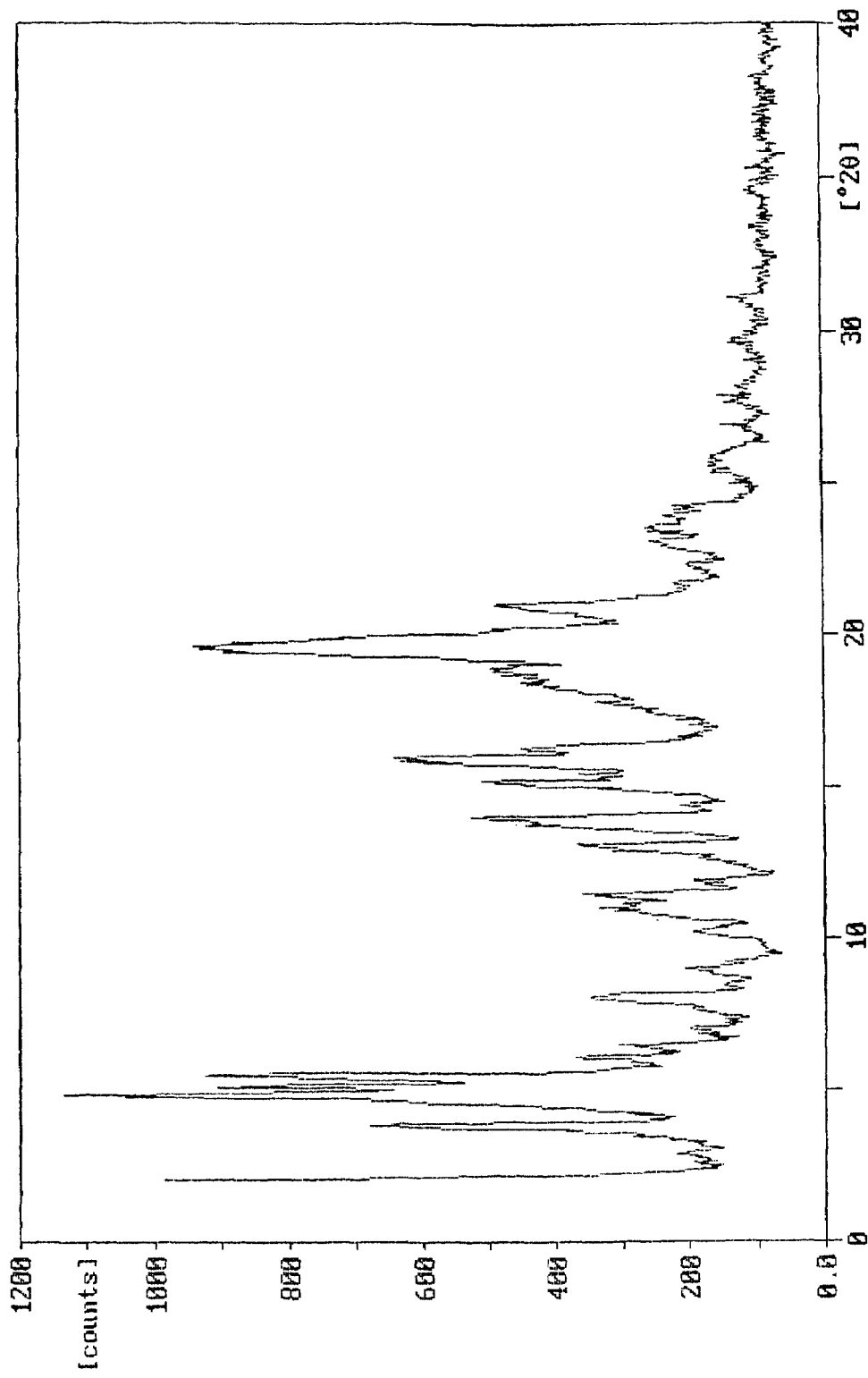

FIG. 13 shows, for comparative purposes, an X-ray powder diffractogram of a mixture of the B-form and the H-form of nateglinide (sample 70/03B), from which it can be seen that that the peak positions (two theta) correspond to both of the diffractograms according to FIGS. 1 and 3 of EP 526 171 and U.S. Pat. No. 5,488,150, respectively.

In the following Appendix 3, there are set out the analytical data recorded by the Philips PW 1710 diffractometer for sample 70/03B and underlying FIG. 13.

What is claimed is:

1. A process for the preparation of nateglinide comprising the following steps:
   i) reaction in a first organic solvent between D-phenylalanine methyl ester or a salt thereof, trans-4-isopropylcyclohexanecarboxylic acid and an acyl chloride or carbonyldiimidazol, to obtain the nateglinide methylester;
   ia) optionally isolating the nateglinide methylester thus obtained and re-dissolving the nateglinide methylester in a second organic solvent, to give a solution;
   ii) addition of water and alkali hydroxide to the reaction mixture coming from step i) without isolating the nateglinide methyl ester, or, if step ia) is carried out, to the solution of step ia), and separation of the aqueous phase containing the alkali salt of nateglinide;
   iii) addition of hydrochloric acid to the aqueous phase coming from step ii), to obtain nateglinide,
   wherein the organic solvent actually employed in step ii) is a solvent non-miscible with water.

2. The process as claimed in claim 1, wherein the first organic solvent employed in step i) is a water-miscible organic solvent, and wherein the isolation of nateglinide methyl ester according to step ia) is carried out through the addition of water to the reaction mixture resulting from step i), and further wherein the second organic solvent employed in step ia) for re-dissolving the nateglinide methylester is non-miscible with water.

3. The process as claimed in claim 1, wherein the first organic solvent employed in step i) is non-miscible with water and wherein step ia) is omitted.

4. The process according to claim 1 wherein the water-miscible organic solvent is selected from the group consisting of acetone, DMF, dimethylacetamide, N-methylpyrrolidone, glyme, diglyme, THF and dioxane.

5. The process according to claim 4, wherein the water-miscible organic solvent is acetone.

6. The process according to claim 1 wherein the organic solvent non-miscible with water is selected from the group consisting of toluene, xylenes, benzene, clorobenzene, methylene chloride, hexane, heptane and cyclohexane.

7. The process according to claim 6 wherein the organic solvent non-miscible with water is toluene.

8. The process as claimed in claim 1, for the preparation of nateglinide in B-form as depicted in the powder X-ray diffractogram in FIG. 11, wherein the addition of hydrochloric acid in step iii) is carried out at a temperature ranging from 5° C. to 20° C.

9. The process as claimed in claim 8, wherein the addition of hydrochloric acid in step iii) is carried out at a temperature ranging from 10 to 20° C.

10. The process as claimed in claim 1, wherein the acyl chloride in step i) is selected from the group consisting of pivaloyl chloride and ethyl chloroformate.

11. The process as claimed in claim 10, wherein the acyl chloride in step i) is pivaloyl chloride.

12. The process as claimed in claim 1, wherein the addition of water and alkali hydroxide in step ii) is earned out in the presence of tri-caprylmethylammonium chloride.

13. The process as claimed in claim 1, wherein the addition of water and alkali hydroxide and the separation of the aqueous phase containing the alkali salt of nateglinide in step ii), is carried out at a temperature ranging from 45 to 55° C.

14. The process as claimed in claim 1, wherein the hydrochloric acid in step iii) is added to the aqueous phase coming from step ii) until a pH comprised between 2.0 and 3.0 is obtained.

15. The process as claimed in claim 1, wherein the D-phenylalanine methyl ester salt in step i) is the D-phenylalanine methyl ester hydrochloride.

16. A process for the preparation of nateglinide in B-form as depicted in the powder X-ray diffractogram in FIG. 11, starting from nateglinide not being in the pure B-form, comprising dissolving nateglinide in water with alkali hydroxide to obtain an aqueous solution, and adding thereto hydrochloric acid at a temperature ranging from 5° C. to 20° C.

17. The process as claimed in claim 16, wherein the addition of hydrochloric acid is carried out at a temperature ranging from 10° C. to 20° C.

18. The process as claimed in claim 16, wherein the hydrochloric acid is added to the aqueous solution of nateglinide alkali salt until a pH comprised between 2.0 and 3.0 is obtained.

19. A process according to claim 1 in which the alkali hydroxide is selected from the group consisting of lithium hydroxide, potassium hydroxide and sodium hydroxide.

20. The process according to claim 19 in which the alkali hydroxide is potassium hydroxide.

21. The process as claimed in claim 9, wherein the addition of hydrochloric acid in step iii) is carried out at a temperature ranging from 15° C. to 20° C.

22. The process as claimed in claim 17, wherein the addition of hydrochloric acid is carried out at a temperature ranging from 15° C. to 20° C.

* * * * *